(12) United States Patent
Martinelli et al.

(10) Patent No.: US 6,252,064 B1
(45) Date of Patent: Jun. 26, 2001

(54) PROCESS TO PREPARE PHARMACEUTICAL COMPOUNDS

(75) Inventors: Michael John Martinelli, Zionsville; Eric David Moher, Indianapolis, both of IN (US)

(73) Assignees: Eli and Company, Indianapolis, IN (US); University of Hawaii, Honolulu, HI (US); Wayne State University, Detroit, MI (US)

( * ) Notice: Subject to any disclaimer, the term of this patent is extended or adjusted under 35 U.S.C. 154(b) by 0 days.

(21) Appl. No.: 09/541,469

(22) Filed: Mar. 31, 2000

Related U.S. Application Data

(63) Continuation-in-part of application No. 09/029,201, filed as application No. PCT/US97/15626 on Sep. 5, 1997, now abandoned.
(60) Provisional application No. 60/025,438, filed on Sep. 6, 1996.

(51) Int. Cl.$^7$ .................. C07D 267/22; C07D 281/18
(52) U.S. Cl. .................................................. 540/454
(58) Field of Search ................................................ 540/454

*Primary Examiner*—Bruck Kifle
(74) *Attorney, Agent, or Firm*—James P. Leeds

(57) ABSTRACT

This invention provides a process for preparing diastereomerically pure cryptophycin compounds.

1 Claim, No Drawings

PROCESS TO PREPARE PHARMACEUTICAL COMPOUNDS

This application is a continuation-in-part of application Ser. No. 09/029,201 filed Feb. 25, 1998, now abandoned, which is a 371 of PCT/US97/15626 filed Sep. 5, 1997 and claims the benefit of U.S. provisional application Ser. No. 60/025,438 filed Sep. 6, 1996.

This invention relates to the fields of pharmaceutical and organic chemistry and provides a process for preparing cryptophycin compounds. Cryptophycin compounds are useful antimicrotubule agents. Such compounds can be useful for the treatment of cancer and neoplasms, and are thus useful pharmaceutical agents.

The cryptophycin compounds are known to exist as the epoxide, styrene, and chlorohydrin with reference to the $R^1$ and $R^2$ substituents in Formula I.

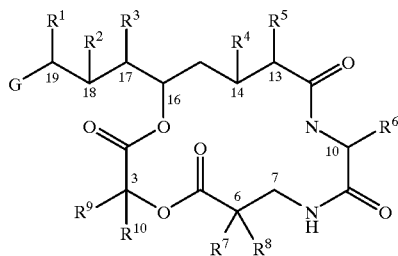

I (substituents defined as in Formula II infra) The synthesis of cryptophycin compounds typically results in the compound Formula I compound wherein $R^1$ and $R^2$ form a second bond (the styrene form). The styrene can be converted to the corresponding epoxide ($R^1$ and $R^2$ together form the epoxide). The epoxide can be stereoselectively opened using a number of nucleophiles, affording an $S_N2$-like inversion at the benzylic position.

However, the corresponding epoxide exists in two diastereomeric forms, as does the corresponding chlorohydrin ($R^1$=Cl; $R^2$=OH). Often only one chlorohydrin diastereomer, such as Formula II infra, is desired.

Unfortunately, the separation of epoxide diastereomers required the use of high performance liquid chromatography. Separations requiring the use of high performance liquid chromatography are generally undesirable for large scale or commercial production of products.

A process of this sort is discussed in *J. Am. Chem. Soc.* 117, 2479 (see P.2483). In this case, a cryptophycin in the styrene form, that is, one in which R1 and R2 are taken to form a double bond between carbons 18 and 19 is converted to an epoxide through the use of m-chloroperbenzoic acid. The epoxide is isolated and separated by HPLC, although the yield is unsatisfactory. Such a process is also disclosed in U.S. Pat. No. 6,013,626 (col. 66, line 35–49).

The present invention provides a process for preparing the chlorohydrin diastereomer of Formula II directly without having to isolate the corresponding epoxide diastereomers. The process not only eliminates a purification step, but it also provides a process wherein the isolation of the desired chlorohydrin can be completed using normal phase/normal pressure chromatography. Thus, the process of this invention provides an efficient one-pot process for the preparation of a diastereomerically pure compound of Formula II:

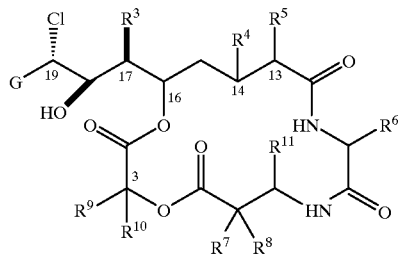

II wherein

G is $C_1$-$C_{12}$ alkyl, or Ar;

Ar is an aromatic or heteroaromatic group or a substituted aromatic or heteroaromatic group;

$R^3$ is $C_1$-$C_6$ alkyl;

$R^4$ and $R^5$ are H; or $R^4$ and $R^5$ taken together form a second bond between C-13 and C-14;

$R^7$ is H, $C_1$-$C_6$ alkyl $NR^{51}R^{52}$, —($C_1$-$C_3$-alkyl)$NR^{51}R^{52}$, $R^8$ is H or $C_1$-$C_6$ alkyl; or $R^7$ and $R^8$ together form a cyclopropyl ring;

$R^{51}$ and $R^{52}$ independently are $C_1$-$C_3$ alkyl;

$R^9$ is H, $C_1$-$C_6$ alkenyl, $C_2$-$C_6$ alkynyl, $C_2$-$C_6$-alkynyl or ($C_1$-$C_6$ alkyl)$C_3$-$C_5$ cycloalkyl;

$R^{10}$ is H or $C_1$-$C_6$ alkyl;

X is O, NH or ($C_1$-$C_3$ alkyl)N—;

Y is C, O, NH, S, SO, $SO_2$ or ($C_1$-$C_3$ alkyl)N—;

$R^6$ is $C_1$-$C_6$ alkyl, substituted ($C_1$-$C_6$)alkyl, ($C_3$-$C_8$) cycloalkyl, substituted $C_3$-$C_8$ cycloalkyl, a heteroaromatic or substituted heteroaromatic group, or a group of formula IIIa, III' or III":

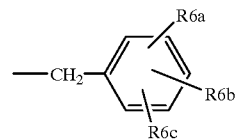

IIIa

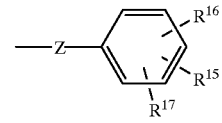

III'

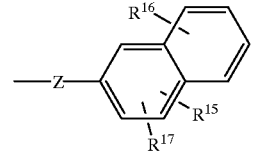

III"

$R^{6a}$, $R^{6b}$, and $R^{6c}$ independently are H, halo or $OR^{18}$;

$R^{15}$, $R^{16}$, and $R^{17}$ independently are hydrogen, halo, ($C_1$-$C_6$) alkyl, $OR^{18}$, O-aryl, $NH_2$, $NR^{18}R^{19}$, $NO_2$, $OPO_4H_2$, ($C_1$-$C_6$ alkoxy)phenyl, Sbenzyl, $CONH_2$, $CO_2H$, $PO_3H_2$, $SO_2R^{23}$, or Z';

$R^{18}$ and $R^{19}$ independently are hydrogen or $C_1$-$C_6$ alkyl;

$R^{23}$ is hydrogen or ($C_1$-$C_3$)alkyl;

Z is —$(CH_2)_n$— or ($C_3$-$C_5$)cycloalkyl;

n is 0, 1, or 2; and

Z' is an aromatic or substituted aromatic group; comprising:

1) reacting a compound of Formula III

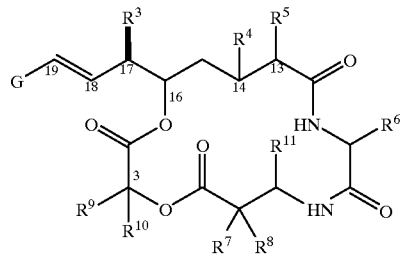

with m-chloroperbenzoic acid (m-CPBA);

2) reacting the reaction mixture with trimethylsilyl chloride; and 3) isolating the Formula II compound using flash chromatography.

The term "flash chromatography" is understood in the art. For example, flash chromatography can be completed using $SiO_2$ as the medium.

The term "alkyl" refers to an alkyl group with the designated number of carbon atoms. It may be saturated or unsaturated, and branched or straight chain. Examples of such alkyl groups include methyl, ethyl, n-propyl, isopropyl, n-butyl, propenyl, sec-butyl, n-pentyl, isobutyl, tert-butyl, sec-butyl, methyl-substituted butyl groups, pentyl, tert-pentyl, sec-pentyl, methyl-substituted pentyl groups and the like.

"Substituted alkyl" refers to a $C_1$-$C_6$ alkyl group that may include up to three (3) substituents containing one or more heteroatoms. Examples of such substituents are OH, $NH_2$, $CONH_2$, $CO_2H$, $PO_3H_2$ and $SO_2R^{21}$ wherein $R^{21}$ is hydrogen, $C_1$-$C_3$ alkyl or aryl.

The term "cycloalkyl" refers to a saturated $C_3$-$C_8$ cycloalkyl group. A "substituted cycloalkyl group" refers to a cycloalkyl group having up to three $C_1$-$C_3$ alkyl, halo, or $OR^{21}$ substituents. The substituents may be attached at any available carbon atom. Cyclohexyl is an especially preferred cycloalkyl group.

"Lower alkoxy" means a $C_1$-$C_5$ alkyl group bonded to an oxygen atom.

The term "halo" refers to Cl, Br, F, or I.

The terms "aromatic group" and "heteroaromatic group" refer to common aromatic rings having 4n+2 pi electrons in a monocyclic or bicyclic conjugated system. The term "aryl" refers to an aromatic group, and the term "aralkyl" refers to an aryl($C_1$-$C_6$-alkyl) group. Examples of aromatic groups are phenyl, benzyl and naphthyl. Heteroaromatic groups will contain one or more oxygen, nitrogen and/or sulfur atoms in the ring. Examples of heteroaromatic groups include furyl, pyrrolyl, thienyl, pyridyl and the like. When the aromatic or heteroaromatic groups are substituted, they may have from one to three independently selected $C_1$-$C_7$ alkyl, $C_1$-$C_6$-alkoxy or halo substituents. The substituents may be attached at any available carbon atom.

Especially preferred heterocyclic groups are

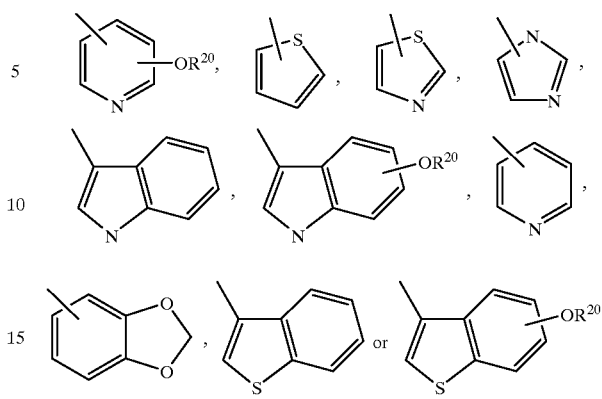

wherein $R^{20}$ is hydrogen or $C_1$-$C_6$ alkyl.

The process of this invention is preferably carried out in the presence of a solvent. The skilled artisan can select appropriate solvents using standard methodologies.

The reaction time is related to the starting materials and operating temperature. The optimum reaction time for a given process is, as always, a compromise which is determined by considering the competing goals of throughput, which is favored by short reaction times, and maximum yield, which is favored by long reaction times.

An especially preferred compound of Formula II is cryptophycin 55 (II). In this process, it is separated from the less preferred isomer, cryptophycin epi-55. These are prepared from the preferred formula III compound cryptophycin 51. The formula II compounds are prepared via epoxide intermediates, such as cryptophycins 52 and 53. The structures of these compounds are as follows:

CRYPTOPHYCIN 51

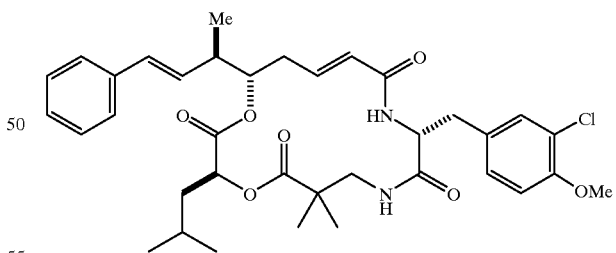

CRYPTOPHYCIN 52

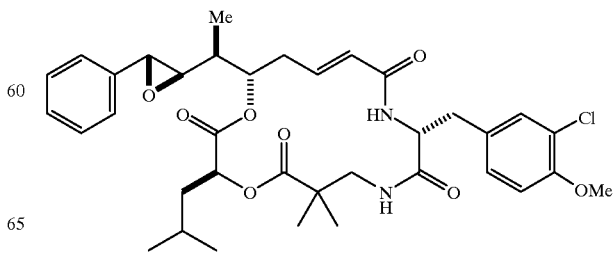

-continued

CRYPTOPHYCIN 53

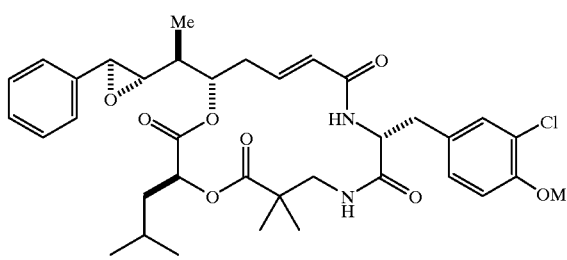

CRYPTOPHYCIN 55

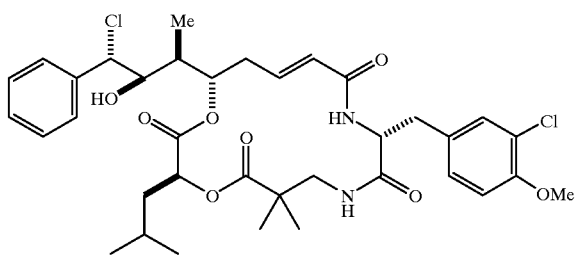

CRYPTOPHYCIN epi-55

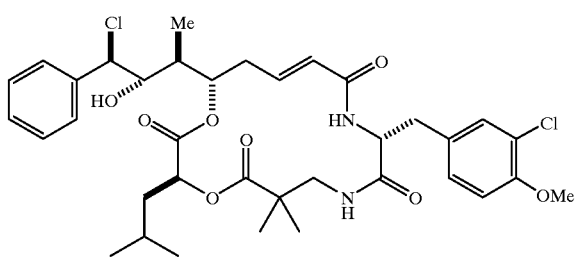

The following example is to illustrate the method of this invention.

EXAMPLE 1

Preparation of Cryptophycin 55

A solution of the olefin cryptophycin 51 (2.15 g, 3.29 mmol) in $CH_2Cl_2$ (11 mL) was cooled to 0° C. under nitrogen. m-CPBA (596 mg, 3.45 mmol) was added, and the solution was allowed to stir at 0° C. for 30 min, then at room temperature for 19.5 h. The reaction mixture was then diluted with $CHCl_3$ (55 mL) and cooled to −60° C. Chlorotrimethylsilane (TMS-Cl) (1.67 mL, 13.2 mmol) was then added dropwise, and the resulting mixture was stirred at the same temperature for 45 min. Another aliqout of TMS-Cl was added with continued stirring for a further 1.5 h. The reaction mixture was concentrated to dryness in vacuo and flash chromatographed over $SiO_2$ with hexane:EtOAc (1:1 to 1:2 to 1:3). Cryptophycin 55 was isolated as a white foam, 1.18 g, 51%.

What is claimed is:

1. A process for preparing a compound of the formula

CRYPTOPHYCIN 55

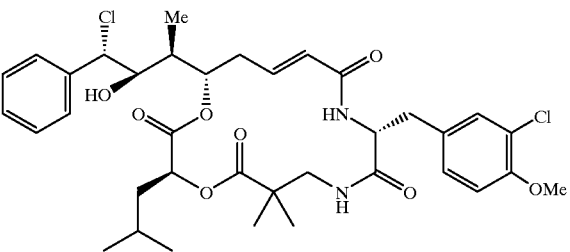

comprising:

1) contacting a compound of the formula

CRYPTOPHYCIN 51

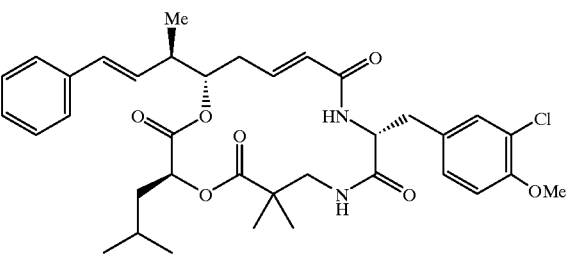

with m-chloroperbenzoic acid;
2) reacting the reaction mixture with trimethylsilyl chloride; and
3) isolating the Cryptophycin 55 compound using flash chromatography.

* * * * *